(12) United States Patent
Grabe et al.

(10) Patent No.: US 9,644,073 B2
(45) Date of Patent: May 9, 2017

(54) METHOD FOR THE SYNTHESIS OF A CHLORINE-FREE, PRE-CERAMIC POLYMER FOR THE PRODUCTION OF CERAMIC MOLDED BODIES

(71) Applicant: BJS CERAMICS GMBH, Gersthofen (DE)

(72) Inventors: Norman Grabe, Augsburg (DE); Michael Rothmann, Munich (DE)

(73) Assignee: BJS Ceramics GmbH, Gersthofen (DE)

( * ) Notice: Subject to any disclaimer, the term of this patent is extended or adjusted under 35 U.S.C. 154(b) by 0 days.

(21) Appl. No.: 14/739,500

(22) Filed: Jun. 15, 2015

(65) Prior Publication Data

US 2015/0274897 A1 Oct. 1, 2015

Related U.S. Application Data

(63) Continuation of application No. PCT/EP2013/076349, filed on Dec. 12, 2013.

(30) Foreign Application Priority Data

Dec. 14, 2012 (DE) .................. 10 2012 223 258

(51) Int. Cl.

| C08G 77/24 | (2006.01) |
| C08G 77/60 | (2006.01) |
| C04B 35/622 | (2006.01) |
| C08G 77/50 | (2006.01) |
| D01F 6/78 | (2006.01) |
| D01F 9/10 | (2006.01) |
| C04B 35/565 | (2006.01) |
| C04B 35/80 | (2006.01) |
| C04B 35/571 | (2006.01) |
| C07F 7/08 | (2006.01) |

(52) U.S. Cl.
CPC ............ *C08G 77/60* (2013.01); *C04B 35/565* (2013.01); *C04B 35/571* (2013.01); *C04B 35/62281* (2013.01); *C04B 35/62295* (2013.01); *C04B 35/80* (2013.01); *C04B 35/806* (2013.01); *C07F 7/0809* (2013.01); *C08G 77/50* (2013.01); *D01F 6/78* (2013.01); *D01F 9/10* (2013.01); *C04B 2235/483* (2013.01); *C04B 2235/5264* (2013.01); *C04B 2235/723* (2013.01); *C04B 2235/724* (2013.01); *C04B 2235/9638* (2013.01); *Y10T 428/2978* (2015.01)

(58) Field of Classification Search
CPC ................. C08G 77/60; C08G 77/50
See application file for complete search history.

(56) References Cited

U.S. PATENT DOCUMENTS

| 4,537,942 A | 8/1985 | Brown-Wensley et al. |
| 4,737,552 A | 4/1988 | Baney et al. |
| 4,889,899 A * | 12/1989 | Bujalski ................ C04B 35/571 |
| | | 525/479 |
| 5,407,987 A * | 4/1995 | Fukushima .............. H01B 1/12 |
| | | 252/500 |
| 5,616,308 A | 4/1997 | Richter et al. |
| 6,020,447 A | 2/2000 | Seyferth et al. |
| 8,466,076 B2 | 6/2013 | Ruedinger et al. |
| 2008/0318158 A1 * | 12/2008 | Takei ................... C09D 183/16 |
| | | 430/272.1 |
| 2011/0045404 A1 * | 2/2011 | Imamura ................ C08G 77/60 |
| | | 430/270.1 |
| 2011/0263780 A1 | 10/2011 | Ruedinger et al. |
| 2013/0011675 A1 | 1/2013 | Clade et al. |

FOREIGN PATENT DOCUMENTS

| EP | 0668254 B1 | 7/1998 |
| WO | 2010072739 A2 | 7/2010 |
| WO | 2011064174 A1 | 6/2011 |

OTHER PUBLICATIONS

Anonymous: "RÖMPP—Polysilane—Georg Thieme Verlag KG", , Apr. 1, 2009 (Apr. 1, 2009), XP055098817, found on the Internet: URL:https://roempp.thieme.de/roempp4.0/do/ data/RD-16-03571 [found on Jan. 28, 2014].
Anonymous: "RÖMPP—Polycarbosilane—Georg Thieme Verlag KG", , Apr. 1, 2009 (Apr. 1, 2009), XP055098818, found on the Internet: URL:https://roempp.thieme.de/roempp4.0/do/ data/RD-16-03135 [found on Jan. 28, 2014].

* cited by examiner

*Primary Examiner* — Margaret Moore
(74) *Attorney, Agent, or Firm* — Laurence A. Greenberg; Werner H. Stemer; Ralph E. Locher

(57) ABSTRACT

A method for producing a polysilane includes a disproportionation reaction of a methylchlorodisilane mixture to form chlorine-containing oligosilane, a substitution reaction of the chlorine atoms contained in the oligosilane by the reaction with a primary amine and a cross-linking reaction of the oligosilanes using a chain former to form polysilanes. The obtained polysilanes are infusible and are very suitable for being spun to form green fibers and processed to form silicon carbide fibers and fiber composites. The method is characterized in that it can be carried out cost-effectively and quickly and with very high yields.

12 Claims, 1 Drawing Sheet

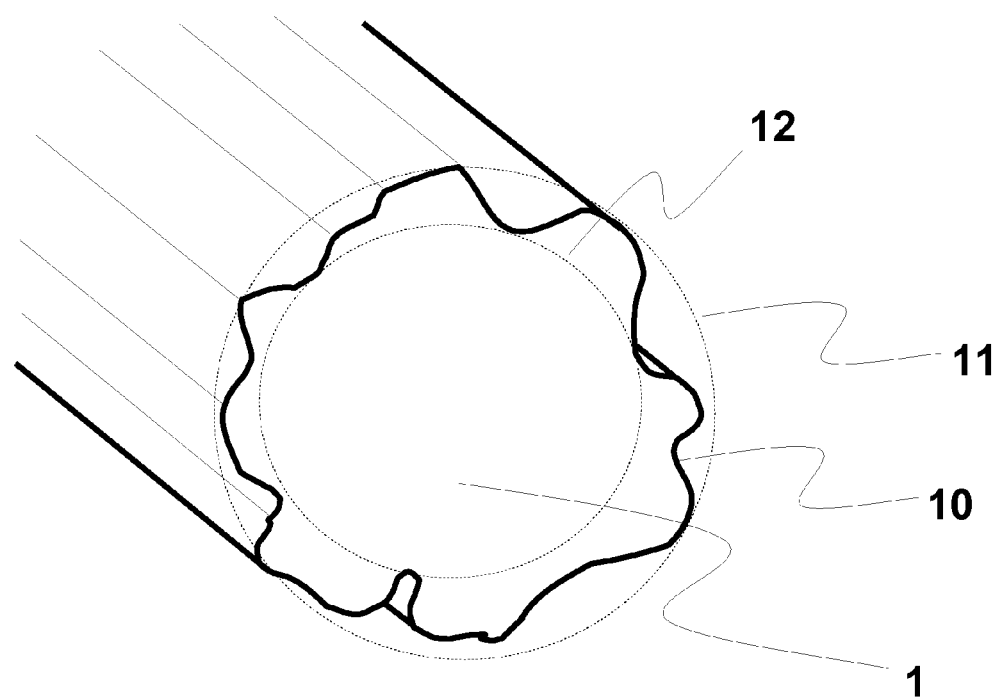

METHOD FOR THE SYNTHESIS OF A CHLORINE-FREE, PRE-CERAMIC POLYMER FOR THE PRODUCTION OF CERAMIC MOLDED BODIES

CROSS-REFERENCE TO RELATED APPLICATION

This is a continuation application, under 35 U.S.C. §120, of copending international application No. PCT/EP2013/076349, filed Dec. 12, 2013, which designated the United States; this application also claims the priority, under 35 U.S.C. §119, of German patent application No. DE 10 2012 223 258.3, filed Dec. 14, 2012; the prior applications are herewith incorporated by reference in their entireties.

BACKGROUND OF THE INVENTION

Field of the Invention

The present invention relates to a method for preparing a chlorine-free, pre-ceramic polysilane, to the chlorine-free and infusible polysilanes themselves and to green fibers and ceramic fibers produced using the polysilane according to the invention, and to the use thereof in silicon carbide-containing moldings or fiber composite materials in lightweight construction, in the semiconductor industry, in the electrical industry, in medical technology, in space travel, in automobile construction and in aircraft construction.

Silicon carbide-containing ceramic components and composite materials are widely used in the semiconductor industry, in electrical engineering, in medical technology, in vehicle and aircraft construction and in space travel due to the hardness, temperature resistance, stability and semiconducting properties thereof.

Silicon carbide-containing ceramic components and composite materials are produced on an industrial scale by preparing a polysilane which is spun into fibers in a melt spinning process. The fibers are then hardened and pyrolysed into ceramic silicon carbide fibers which can then be further processed into ceramic components or composite materials.

The polysilane is firstly prepared by a Wurtz coupling in which an organohalogen silane, such as dichlorodimethylsilane is reacted with molten sodium to produce a polydimethyl silane. A polysilane of this type can be processed into green fibers which can be pyrolysed into silicon carbide fibers. However, a fundamental disadvantage is the complex synthesis of the starting polymer which includes the use of alkali metals, reactions in an autoclave and a laborious extraction process.

A more economical starting material for the polysilane preparation is provided by methylchlorodisilane mixtures, which can be obtained as waste products from the Müller-Rochow synthesis. These mixtures can be disproportionated into oligosilanes under homogeneous or heterogeneous catalysis. European patent EP 668254 B1, corresponding to U.S. Pat. No. 5,616,308, discloses a thermal aftertreatment to prepare polysilanes and the conversion thereof into silicon carbide fibers, which, however, are easily fusible and therefore have to be hardened before pyrolysis, for example using ammonia. Other hardening methods, for example with oxygen, result in an increased introduction of oxygen into the fiber, which greatly impairs the high temperature stability thereof.

To prevent oxygen being introduced into the fibers or generally to avoid carrying out laborious hardening processes, it has been proposed to disproportionate the methylchlorodisilane mixtures from the Müller-Rochow synthesis into oligosilanes under catalysis with Lewis bases and to specifically crosslink them thermally so that they become infusible and therefore do not have to be hardened. However, a disadvantage of these fibers is that they have a very high chlorine content (between 8 and 12% by mass), which makes them susceptible to corrosion. Although the chlorine content can be reduced by a thermal treatment at approximately 1,800° C., the fiber is severely damaged thereby. In addition, exchanging the chlorine for reactive gases such as hydrogen or ammonia leads to a reduction in the mechanical strength of the fibers.

For this reason, it has been proposed in international patent disclosure WO 2010072739, corresponding to U.S. Pat. No. 8,466,076, to react the product of the disproportionation reaction with a substitution agent so that the bound chlorine is replaced by a chlorine-free substituent. The substituted product can then be processed by thermal cross-linking into a chlorine-free polysilane which does not contain any oxygen and can be further processed into silicon carbide fibers. However, this thermal post-cross-linking is cost-intensive and not easily reproduced and should be avoided. Furthermore, after thermal post-cross-linking, the yield of polysilane is relatively low, inter alia because after cross-linking, the polysilane has to be re-dissolved and insoluble product is lost. In addition, highly reactive cleavage products are produced during the thermal cross-linking of the dechlorinated oligosilanes. These products have to be removed in a technically complex manner. Unfortunately, without a satisfactory alternative to thermal post-cross-linking, further processing of the polysilane is not possible since the polymer needs a high molecular weight in order to be suitable for the spinning process.

SUMMARY OF THE INVENTION

It is therefore the object of the present invention to provide an economical and reproducible method with a high yield for the preparation of chlorine-free and infusible yet soluble polysilanes which can be used in an outstanding manner for the production of green fibers and ceramic fibers, and the green and ceramic fibers produced therefrom.

The object is achieved according to the invention in that a method for preparing a polysilane is provided which contains the following steps:
(i) a disproportionation reaction of a methylchlorodisilane mixture to produce a chlorine-containing oligosilane,
(ii) a substitution reaction of the chlorine atoms contained in the oligosilane by reacting with a primary amine, and
(iii) a cross-linking reaction of the oligosilanes using a chain forming agent to produce polysilanes.

This achievement of the object produces an almost chlorine-free polysilane (less than 1% chlorine content, preferably less than 0.3% chlorine content) in a very high yield. Furthermore, the method is economical and fast and can be carried out at low reaction temperatures. Condensates, which would have to be removed, do not form during the reaction, and therefore this production procedure of polysilane is not critical in terms of safety even when large quantities of polysilane are produced. The polysilanes can be processed in an outstanding manner into green fibers and are infusible at the processing temperatures. The polysilanes are very soluble so that a high yield can also be achieved for further processing into green fibers.

The methylchlorodisilane mixture is preferably a mixture of 1,1,2,2-tetrachlorodimethyldisilane and 1,1,2-trichlorotrimethyldisilane with preferably less than 10 mol. % of other constituents, which is a by-product of the industrially applied used Rochow and Müller synthesis, meaning that the starting mixture of the present reaction is an economical starting material. In general, the methylchlorodisilanes used are characterized in that they preferably have a composition of $Si_2Me_nCl_{6-n}$, where n can be 1, 2, 3 or 4.

It is preferred that the mentioned methylchlorodisilane mixtures are disproportionated under homogeneous catalysis with a nitrogen-containing Lewis base and preferably at an elevated temperature, the monosilane mixtures produced as cleavage products during the reaction being continuously distilled off. The reaction temperature is preferably from 150-300° C., more preferably from 200-250° C. The catalyst used is an organic nitrogen compound with Lewis basicity but without an N—H function. Preferred catalysts are nitrogen-containing heterocycles such as pyridine, quinoline, N-methylpiperidine, N-methylpyrrolidine, N-methylindole or N-methylimidazole. The quantity of catalyst used is preferably from 1 to 2% by mass. Disproportionation is carried out under the conditions known in the patent literature (see for example international patent disclosure WO 2010072739). It is particularly favorable to keep moisture and oxygen away from the materials using inert gas, such as high purity nitrogen gas, because the product is sensitive to oxygen. The addition of a cross-linking aid has proved to be particularly advantageous for the preparation of the oligosilane. This cross-linking aid can be an aryl halogen silane, an aryl halogen borane or a mixture of these compounds. Phenyltrichlorosilane, diphenyldichlorsilane and phenyldichlorborane are preferably used as cross-linking aids, more preferably phenyltrichlorosilane. The quantity of the cross-linking aid used during the disproportionation reaction is preferably from 5 to 20% by mass, more preferably from 10 to 15% by mass.

The chlorine substitution, step (ii) in the preparation process of the polysilane, is carried out on the product of the disproportionation or of a comparable reaction to produce a crude oligosilane in order to reduce the quantity of chlorine. The chlorine is reduced by substituting chlorine atoms using amine and/or silylamine compounds, i.e. compounds which have at least one N—Si group or, more preferably, at least one N—H group. In a first embodiment of the invention, they are preferably selected from ammonia and primary or secondary amines. Particularly suitable are amines of formula $HNR^1R^2$, where $R^1$ and $R^2$, independently of one another, represent hydrogen, alkyl, alkenyl, aryl, arylalkyl, alkylaryl, arylalkenyl, alkenylaryl optionally substituted with further amino groups, or $(R^3)_3Si—[NR^3—Si(R^3)_2]_m$ where m=0 to 6, or where $R^1$ and $R^2$ together represent an alkylene functional group having 4 or 5 carbon atoms or $—Si—(R^3)_2[NR^3—Si(R^3)_2]_n$ where n=1 to 6. In a second embodiment, silyl amines, in particular silazanes of formula $Si—(R^3)_3[NR^3—Si(R^3)_2]_nR^3$ are used, where n can be a whole number from 1 to 6. Every functional group $R^3$ is in all cases the same or different and represents hydrogen, alkyl or aryl. In a third, preferred embodiment, the compounds are secondary cyclic amines, particularly selected from pyrrole, indole, carbazole, pyrazole, piperidine and imidazole. In a fourth embodiment, substitution takes place with a compound of formula $N(R^4)_3$, where $R^4$ means $(R^3)_3Si$.

The number of amino groups in $R_1$ and $R_2$ is not restricted, but is preferably from 0 to 6 and more preferably from 0 to 4. The number of carbon atoms in $R_1$, $R_2$ and $R_3$ is also not restricted, but is preferably from 1 to 6 for aliphatic functional groups and from 5 to 20 for aromatic and aliphatic-aromatic functional groups.

More preferably, the amines are selected from ammonia, ethylene diamine, diethylamine, dimethylamine, methylamine, aniline, ethylamine, hexamethyldisilazane, heptamethyldisilazane and tris-(trimethylsilyl)amine. Of the above-mentioned amines, the amines which carry short-chain alkyl functional groups, in particular methyl and ethyl functional groups, are particularly preferred. Dimethylamine is particularly favorable. Secondary amines have the advantage that the polymers obtained thereby carry $—NR^2$ groups, in other words they are free from NH functions. The advantage is that during the subsequent cross-linking of such polysilane/oligosilanes substituted in this manner, polycondensation of amino groups is impossible, which could produce products which are more difficult to dissolve or are no longer soluble, which is naturally undesirable according to the invention. However, silylamines such as disilazanes instead of pure amines are also suitable, since the introduction of silicon atoms during substitution does not present any disadvantageous effects for the later moldings or fibers. Substitution with silylamines also has the advantage that the chlorine does not occur as an ammonium salt, but rather as trimethylchlorosilane which can be separated by distillation and returned into the process chain.

Chlorine reduction/substitution is usually carried out as now described.

The starting material, i.e. the crude polysilane/oligosilane which carries/contains hydrocarbon groups and is obtained by the above-described disproportionation is dissolved in a suitable inert and aprotic solvent. Possible solvents include in particular aprotic, non-polar solvents such as aliphatic hydrocarbons (for example n-pentane, n-hexane, cyclohexane, n-heptane, n-octane), halogenated hydrocarbons (for example methylene chloride, chloroform, carbon tetrachloride, 1,1,1-trichloroethane, chlorobenzene) or aromatic hydrocarbons (for example benzene, toluene, o-xylene, symmesitylene), also ether-containing solvents (for example diethylether, diisopropylether, tetrahydrofuran, 1,4-dioxane or a higher or asymmetrical ether). The solvent is preferably a halogen-free hydrocarbon, more preferably an aromatic hydrocarbon from the group of benzene, toluene, o-xylene.

The substitution agent (amine) is added in a molar excess which is preferably at least 2:1, based on the bound chlorine atoms in the starting material. The substitution agent is added undiluted or dissolved in an inert and aprotic solvent, as stated above. For example it can be added drop wise; while so doing, a temperature between room temperature and the boiling point of the amine or of the solution thereof should preferably be observed. During or after the drop wise addition, a salt forms which is insoluble in the solvent or, in the case of substitution with silyl amines, trimethylchlorosilane forms. The suspension is left to stand for some time, often for several hours or is boiled under reflux to boiling point of the solvent. It is then optionally cooled to room temperature and if salt has formed, the salt is filtered off. Thereupon, the solvent and optionally formed trimethylchlorosilane is completely removed, for example under vacuum.

When an amine is used which is present as a gas during the addition of crude polysilane/oligosilane, for example when ammonia is used, the amine can be introduced as gas or condensed into a reaction vessel either at temperatures below its boiling point or introduced into the vessel as a liquid under excess pressure, in the case of liquefied amines optionally diluted with a suitable solvent, as stated above. The starting material is then added, again dissolved as far as possible in the same solvent. Following addition, the batch is left to stand for a similar time period as stated above or boiled under reflux and then worked up as described above.

The chlorine content of the starting material treated thus can usually be reduced to less than 0.2% by mass by the method step according to the invention.

The cross-linking step (iii) of the invention produces polysilanes using a chain forming agent. The chain forming agent preferably has at least two nucleophilic groups.

Preferably used as chain forming agents are one or more of the compound classes of diamines, triamines, dioles and/or trioles, as well as polyamines, polyols and/or polythiols. The use of these chain forming agents produces an effective cross-linking of the oligosilanes, in large yields at a low reaction temperature and with a short reaction duration and in a high-quality polysilane. Amino groups are preferred as nucleophilic groups. Diamines and/or triamines are preferably used.

More preferably used as chain forming agents are one or more of the compounds: 1.6-diaminohexane, 1,4-diaminobutane, 1,2-ethylene diamine, melamine, triethylene diamine, glycerine and/or triethanolamine. 1,6-diaminohexane in particular led to high yields at a low reaction temperature and with short reaction times.

The chain forming agent is preferably used in a concentration of from 1 to 40% by mass, more preferably from 1 to 20% by mass and most preferably from 1 to 10% by mass compared with the oligosilane. A concentration of this type results in an optimum cross-linking with the desired molecular weight and viscosity of the polysilane product.

In particular, it is surprisingly possible, compared with thermal post-cross-linking, to carry out the cross-linking reaction at a moderate temperature within a range preferably of from 50 to 150° C. and more preferably within a range of from 65 to 120° C. and even more preferably within a range of from 100 to 112° C. The necessary time for the post-cross-linking can also be reduced. This time is preferably from 1 to 3 hours.

Due to the particularly preferred temperature range, it is preferred to use toluene as the solvent for the cross-linking reaction, especially as the use of toluene produces very high yields of almost 100% because the polysilanes obtained in the cross-linking reaction are very soluble in toluene. Further suitable solvents are tetrahydrofuran, dioxane, benzene, xylene and other aprotic organic solvents.

The invention also includes a polysilane which is prepared according to the present invention, and a method for producing silicon carbide fibers.

The polysilane preferably has a molecular mass (Mw) of more than or equal to 2,000 g/mol. Furthermore, the polysilane preferably has a molecular weight Mw of from 1,000 to 10,000 g/mol, preferably from 2,000 to 4,000 g/mol, most preferably from 2,500 to 3,500 g/mol and a bimodal molecular weight distribution.

The molecular weight (Mw) is preferably determined by gel permeation chromatography.

Furthermore, in the polysilanes according to the invention, the polydispersity is from 1 to 5, preferably from 1.5 to 4, most preferably from 2.5 to 3.5, which is achieved by a specifically bimodal molecular weight distribution. The bimodality can be achieved in that not all the oligosilane molecules are incorporated in the polymer. The more chain forming agent is used, the more oligosilane is reacted, consequently a higher molecular weight of the polymer is obtained and at the same time the polydispersity is increased. This applies to the quantity, stated here, of chain forming agent which is used.

The method according to the invention for producing silicon carbide fibers is preferably characterized in that the polysilanes prepared according to the invention are spun into polysilane fibers and the polysilane fibers are converted into silicon carbide fibers by pyrolysis and optionally preferably by sintering. Pyrolysis and sintering can be carried out according to any protocol known to a person skilled in the art.

The polysilane according to the invention is preferably processed into fibers in the dry spinning process. However, the polysilane according to the invention can also be processed in the wet spinning process.

In principle, the dry spinning process can be carried out in any manner known to a person skilled in the art. Possible solvents for the polysilane are in particular organic solvents such as aliphatic hydrocarbons (for example n-pentane, n-hexane, cyclohexane, n-heptane, n-octane), aromatic hydrocarbons (for example benzene, toluene, o-xylene, sym-mesitylene), haologenated hydrocarbons (for example methylene chloride, chloroform, carbon tetrachloride, 1,1,1-trichloroethane, chlorobenzene) or ethers (for example diethylether, diisopropylether, tetrahydrofuran, 1,4-dioxane or a higher or asymmetrical ether). The solvent is preferably a halogenated or halogen-free hydrocarbon, more preferably a halogen-free aromatic hydrocarbon from the group of benzene, toluene, o-xylene.

A stable spinning procedure is possible in the dry spinning process due to the excellent solubility thereof. Consequently, thinner fiber diameters can be obtained and fewer fibers break in the spinning process. The polysilanes according to the invention also exhibit good elasticity which makes them eminently suitable for the spinning process.

Due to its high quality, the polysilane can be spun particularly effectively into fibers.

In particular, the polysilane according to the invention has very good solubility, even at high concentrations of from 70 to 90 wt. % in the solvent. Since at concentrations of from 70 to 90 wt. % in toluene or dioxane it simultaneously has a low viscosity at 30° C. of from 50 to 150 Pas at the processing temperature, the polysilane according to the invention can thus be processed in a high concentration.

The polysilane preferably has a viscosity at 25° C. in a 50 wt. % solution in toluene of from 5 to 50 mPas, preferably from 15 to 30 mPas. Such low viscosity values are advantageous for dry spinning because the polysilane can be processed more easily.

The high-quality fibers obtained therefrom can then be directly pyrolysed into SiC ceramics without having to be hardened. However, it is clear to a person skilled in the art that the fibers which are obtained can be hardened. Therefore, the fibers produced according to the invention are distinguished in that they do not have to be hardened, although alternatively they can be hardened. A person skilled in the art can measure the viscosity using known methods from the prior art.

For a further quality control of the spinnability of the polysilane, a dry spinning process was carried out with a viscosity of the polysilane from 10 to 160 Pas. The fiber filament reduction per hour in percent was determined as a further quality parameter in addition to the solubility of the polysilane. This value describes the reduction rate in the number of filaments in the fiber bundle during dry spinning and is calculated from the quotient of the filament number at time n and from the filament number at time n minus 1 hour in the fiber bundle. In this respect, the filament number was determined optically and was recorded. The polysilane according to the invention and the preparation method thereof are preferably characterized in that the fiber filament reduction per hour has a value of from 0 to 75%, preferably from 0 to 60%, more preferably from 0 to 40%, even more preferably from 0 to 30% and even more preferably from 0 to 20%. Comparative measurements with polysilane from the prior art produced fiber filament reduction values of 80%. Thus, the polysilane according to the invention and the preparation method thereof result in lower fiber filament reductions than the prior art. It is preferably possible to spin the polysilane according to the invention into fibers during dry spinning with draw factors of at least 6, preferably at least 7, most preferably at least 8. It is particularly preferred that the draw factors have a value of from 5 to 10, preferably from 6 to 8. It is advantageous here to use high draw factors because it is then possible for thinner filaments to be produced using the same nozzle diameter. The draw factor is calculated from the ratio of the exit area of the nozzle and the cross-sectional area of the fibers. Thinner filaments are attractive for the later processing of the fibers, thus the use of higher draw factors is desirable which is now possible through the use of the polysilane according to the invention.

Dry spinning is preferably carried out on a spinning apparatus, consisting of a feed vessel, a gear pump and a nozzle head at a temperature of 30° C., using a spinneret of diameter 75 µm. The resulting pressures range from 5-250 bars. The spinning chamber contains a nitrogen atmosphere at 30° C. Draw factors from at least 6-8 can be realized at a take-off rate of from 50-200 m/min.

Due to the infusibility of the polysilanes according to the invention, the polysilane fibers can be processed into silicon carbide fibers by pyrolysis and preferably by subsequent sintering, without being melting in the process.

Thus, a further aspect of the present invention is a silicon carbide fiber, starting from the polysilane according to the invention, or fibers produced by pyrolysis of the polysilane fibers and preferably by subsequent sintering. Surprisingly, it has been found that the polysilane fiber has a surface structure which is different from known polysilane fibers and furthermore that this surface structure is retained in the silicon carbide fiber produced from the polysilane fiber according to the invention. The silicon carbide fiber according to the invention has a characteristic, non-circular cross-sectional surface. This surface structure has the advantage that the infiltration of a fiber material, consisting of the silicon carbide fibers, by a liquid matrix material produces a relatively close bond because fewer gas inclusions remain or occur during infiltration. Without wishing to be tied to the theory, this is because the fibers do not form a close contact surface, or they form a contact surface of a relatively low tightness amongst one another.

Other features which are considered as characteristic for the invention are set forth in the appended claims.

Although the invention is illustrated and described herein as embodied in a method for the synthesis of a chlorine-free, pre-ceramic polymer for the production of ceramic molded bodies, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWING

The single FIGURE of the drawing is an illustration of a silicon carbide fiber according to the invention.

DETAILED DESCRIPTION OF THE INVENTION

Referring now to the single FIGURE of the drawing in detail thereof, there is shown an embodiment of the silicon carbide fiber according to the invention that has a cross-sectional surface 1. Accordingly, a preferred silicon carbide fiber has the cross-sectional surface 1 with an undulating boundary line 10. The degree of undulation can be described as follows. The FIGURE shows the undulating cross section 10, an outer sheathing circle 11 as well as the largest possible circular surface 12 inside the fiber cross-sectional surface 1. The outer circular surface 11 is at least 5%, preferably at least 10%. In this respect, the curvature of the boundary line 10 repeatedly changes sign. At least two radii of curvature with different signs have an amount of at least 1 µm in each case. A simple oval fiber cross section is not included by the cross section according to the invention; on the other hand an undulating but basically oval cross-sectional surface is included by the cross-sectional surface according to the invention.

The polysilane preferably has a ceramic yield of at least 60% during pyrolysis up to 800° C. Here, the ceramic yield is defined as residual mass after pyrolysis under protective gas at 800° C. at a heating rate of 10 K/min. Therefore, after pyrolysis, the polysilane according to the invention has a very good yield.

In principle, pyrolysis or sintering can be carried out in any manner known to a person skilled in the art and with any temperature profile. However, good results are particularly obtained when pyrolysis is carried out with the exclusion of oxygen, i.e. under an inert gas atmosphere such as nitrogen so that the maximum temperature is from 400 to 1200° C., preferably from 600 to 1,000° C. and more preferably from 800 to 900° C. During pyrolysis, the heating rate is set at a value between 0.1 and 200 K/min, preferably between 0.5 and 50 K/min, more preferably between 0.75 and 10 K/min and most preferably at a value of approximately 1.0 K/min. At from 400 to 500° C., the conversion of the polysilane into the silicon carbide is complete. Sintering is preferably carried out at temperatures between 800 and 2,000° C. under an inert gas atmosphere, such as preferably under argon, nitrogen or a nitrogen-hydrogen mixture, and at heating rates of from 1 to 150 K/min. This has the advantage that by increasing the temperature, but still below the melting temperature, the polymer structure changes and the mechanical properties of the fiber are improved. During sintering, the individual fibers do not bind on to each other.

The silicon carbide ceramic according to the invention has an element composition of from 20 to 45 wt. %, preferably from 23 to 40 wt. % of carbon, from 5.0 to 8.0 wt. % of nitrogen, from 0.0 to 4.0 wt. % of oxygen, from 0.0 to 2.0 wt. % of chlorine and from 48 to 72 wt. % of silicon.

According to an embodiment, the silicon carbide ceramic according to the invention in the form of silicon carbide fibers has an element composition of from 38 to 40 wt. % of carbon, from 7.0 to 8.0 wt. % of nitrogen, from 2.0 to 3.0 wt. % of oxygen, from 1.0 to 1.5 wt. % of chlorine and from 48 to 50 wt. % of silicon.

The invention also includes a fiber composite material, characterized in that it contains a silicon carbide fiber according to the invention and a matrix material.

Likewise, the polysilane fibers produced according to the invention can be used in a fiber composite material, characterized in that the fiber composite material contains a polysilane fiber according to the invention and a matrix material. If appropriate, the polysilane fiber is converted into a ceramic fiber by a treatment, preferably by pyrolysis of the fiber composite material.

In this respect, the fibers or matrix can be composed of the silicon carbide according to the invention and of the substance systems SiC, SiCN, SiBNC, $Al_2O_3$, $SiO_2$, $TiO_2$, $ZrO_2$ (and mixtures thereof), it being preferred for the fibers and the matrix to be composed of the silicon carbide according to the invention.

Furthermore, the polymer fibers or ceramic fibers can be provided in the form of non-crimp fabrics, fiber mats, woven fabrics, warp-knitted fabrics, weft-knitted fabrics, nonwoven fabrics and/or felts, non-crimp fabrics and/or fiber mats being preferred.

To produce the composite material according to the invention, silicon carbide fibers produced as above or other fiber structures containing other ceramic fibers, preferably SiCN fibers, can be impregnated with the polysilane described according to the invention or with other polymer precursors and then pyrolysed. This means that the fibers and the matrix of the composite material according to the invention can be composed of the silicon carbide according to the invention. Further other possible substance systems for fibers or matrix are SiCN, SiBNC, $Al_2O_3$, $SiO_2$, $TiO_2$, $ZrO_2$ and mixtures thereof, it being preferred for the fibers and the matrix to be composed of the silicon carbide according to the invention.

A hardening procedure can optionally be carried out between impregnation and pyrolysis, which hardening can be carried out in a physical or chemical manner, for example using UV light and/or by a temperature treatment. Thereafter, the body produced thus can be impregnated once or several times with polysilane, hardened and pyrolysed.

Furthermore, the described polysilane can be applied as a solution to any fibers or moldings and, after pyrolysis, it forms a protective layer, for example an oxidation protective layer. Due to its outstanding characteristics, in particular its outstanding high temperature resistance and high degree of hardness, the polysilane according to the invention, the silicon carbide fiber according to the invention and silicon carbide moldings which have been produced and silicon carbide-containing fiber composite materials according to the invention, moldings according to the invention and/or fiber composite material are particularly suitable for uses in which the material is exposed to elevated temperatures and oxidative conditions, specifically for example in lightweight construction, in the electrical industry, in space travel, in automobile construction and in aircraft construction.

EXAMPLES

In the following, the present invention is described on the basis of practical examples according to the invention in comparison with a comparative example which has been carried out without a cross-linking reaction but with a thermal cross-linking, the practical examples describing the present invention without restricting it. The comparative example and the practical example are compared with one another in respect of the necessary reaction temperature, time and yield. In addition, in Table 1, the concentration of polysilane which can be used for dry spinning, i.e. the concentration of polysilane which is still dissolving, the viscosity, spinnability and the pyrolysing characteristic of the polysilane for the polysilane of the invention according to Example 1, for the comparative example and for the oligosilane are compared with one another.

The viscosity of the polysilane or of the spinning masses was determined using a rotation rheometer Physica MCR 301 manufactured by Anton Parr. The measurements were made using a plate/plate geometry with approximately from 300-500 mg of the respective sample. The viscosity of the diluted polymer solutions was measured on a falling-ball viscosimeter manufactured by HAAKE at 25° C. in 50% solution with a 16.25 g steel ball.

Comparative example from the prior art according to international patent disclosure WO 2010072739:

The comparative example was produced in three steps, namely first the preparation of an oligosilane, second the modification of the oligosilane with gaseous dimethylamine and third the thermal cross-linking of a dimethylamine-modified oligosilane.

Step 1: Preparation of an Oligosilane by Disproportionation 600 g of a methylchlorodisilane mixture ("disilane fraction" from a Müller-Rochow process, consisting of respectively 45 mol. % $Cl_2MeSiSiMeCl_2$ and $Cl_2MeSiSiMe_2Cl$ as well as 10 mol. % $ClMe_2SiSiMe_2Cl$; by 150-155° C.) are mixed with 14 g N-methylimidazole and 69 g phenyltrichlorosilane and heated to 180° C. at 0.5 K/min. Approximately 450 ml of a distillate are obtained consisting of $MeSiCl_3$, $Me_2SiCl_3$ and $Me_2ClSiSiMe_2Cl$, as well as 153 g of a dark brown hydrolysis-susceptible oligosilane which is solid at room temperature and has a chlorine content of approximately 25% by mass. This is dissolved in toluene or xylene to produce a 60% by mass solution containing oligosilane.

Step 2: Modification of an Oligosilane Using Gaseous Dimethylamine

Introduced into a double-wall 2-L reaction vessel with a bottom valve, reflux cooler, KPG stirrer, internal thermometer and gas inlet tube are 1,500 ml of a 60% solution of an oligosilane obtained by disproportionation of the "disilane fraction" in toluene or xylene, which solution is then cooled to 0° C. Thereafter, approximately 700 g of gaseous dimethylamine are introduced under the liquid level with vigorous stirring within 3 hours. In so doing, the temperature of the mixture rises to 30-35° C. and falls again towards the end of the reaction. The product is removed via the bottom valve under pressurized argon and the separated dimethylammonium chloride is filtered off via a pressure nutsche filter. The solvent is distilled off from the filtrate. The modified oligosilane still contains approximately 1.5-2% by mass of chlorine.

Step 3: Thermal Cross-Linking of a Dimethylamine-Modified Oligosilane 600 g of the modified oligosilane are slowly heated in a distillation apparatus to an end temperature of approximately 400° C. During the heating procedure, approximately 200 ml of a yellowish distillate are obtained; the solidification of the mass indicates the end point of cross-linking. After cooling, the copolymer which is obtained, the chlorine content of which is now only approximately 0.5% by mass, is dissolved in toluene and can be used in a dry spinning process for the production of green fibers.

The yield of polysilane is rounded off at 60%. During thermal cross-linking, temperatures of above 300° C. are required, the reaction lasts 4-6 hours. The viscosity of the polysilane is 100 Pas at 30° C. The concentration of polysilane which can be used for dry spinning is 70%. The polysilane is spinnable and immediately pyrolysable.

Practical Example

The first and second steps of the polysilane preparation, namely the disproportionation and the modification using gaseous dimethylamine according to international patent disclosure WO 2010072739 (see comparative example) can be carried out for the preparation of a polysilane according to the invention. The third step of the preparation process, thermal cross-linking according to WO 2010072739, is not carried out according to the invention. Instead, polymerisation takes place by cross-linking with a chain forming agent. According to the invention, the cross-linking reaction can take place in accordance with the now described protocol.

1400 g of oligosilane solution (chlorine-free, 57%) are introduced into a 2 L flat flange vessel, fitted with a reflux cooler, an argon connection and an anchor stirrer. The reactor was previously rendered inert by applying a vacuum for 30 minutes and was flooded with argon. 70 g of 1,6-diaminohexane (hexamethylenediamine, HMDA) as chain forming agent are dissolved in 233.3 g toluene while being heated (40° C.).

This solution is added to the oligosilane over a period of 2 minutes at room temperature in an argon counter flow while being stirred (108 rpm). To remove the resulting dimethylamine (DMA), a light stream of argon (5 cm3/min) is passed into the vessel and through the cooler.

The reaction is started by heating the solution to reflux within a period of from 20-30 minutes. After reaching the reflux temperature (approximately 111° C.), the solution is stirred for a further 2 hours (108 rpm).

At the end of the reaction time, the solution is cooled and degassed at 100 mbar for 10 minutes at 30° C. The solution is then filtered over a 1 μm depth-filter with 3 bars nitrogen pressure.

The polysilane according to the invention is obtained in a yield of 95%. In this example, the maximum reaction temperature in the cross-linking step is 111° C. The reaction duration is 2 hours. Compared with the prior art, the yield is significantly higher, the reaction duration is shorter and the reaction temperature in the last step is lower. Therefore the method is more economical and faster. The viscosity is 100 Pas at 30° C. The concentration of polysilane which can be used for dry spinning is 85% and thus is higher than in the comparative example. Furthermore, the polysilane is spinnable and immediately pyrolysable. The oligosilane, however, is neither spinnable nor pyrolysable.

TABLE 1

| | Oligosilane acc. to step 2 of comparative example | Comparative example | Practical example |
|---|---|---|---|
| Concentration (wt. %) of polysilane which can be used for dry spinning | 70% | 70% | 85% |
| Viscosity at 30° C. | <1 Pas | 100 Pas | 100 Pas |
| Spinnable | No | Yes | Yes |
| Immediately pyrolysable | No | Yes | Yes |

Practical Example 2

The reaction of practical example 2 is carried out analogously to that of practical example 1. Instead of HMDA, 1,2-ethylendiamine is used as chain forming agent.

Practical Example 3

The reaction of practical example 3 is carried out analogously to that of practical example 1. Instead of HMDA, melamine is used as chain forming agent.

Practical Example 4

The reaction of practical example 4 is carried out analogously to that of practical example 1. Instead of HMDA, triethylenediamine (TREN) is used as chain forming agent.

Practical Example 5

The reaction of practical example 5 is carried out analogously to that of practical example 1. Instead of HMDA, glycerine is used as chain forming agent.

Practical Example 6

The reaction of practical example 6 is carried out analogously to that of practical example 1. Instead of HMDA, triethanolamine is used as chain forming agent.

Practical Example 7

The reaction of practical example 7 is carried out analogously to that of practical example 1. Instead of the stated concentration of HMDA, it is also possible to use from 1-20 mol. % of HMDA.

Practical Example 8

Processing in the Dry Spinning Process

The polysilane prepared according to the invention is processed into green fibers by dry spinning. For this purpose, the polysilane is dissolved in toluene, THF or dioxane and conveyed by a pump at 30° C. through the spinneret having a diameter of 75 μm. The resulting pressures are from 5-250 bars. The spinning-column contains a nitrogen atmosphere at 30° C. At a take-off rate of from 50-200 m/min, draw factors of at least 6-8 can be realized. It is possible to obtain suitable green fibers for the subsequent steps.

Practical Example 9

Pyrolysis

The hardened fibers are pyrolysed under a protective gas atmosphere up to 1,200° C. The heating rate is 10 K/min. At 400 to 500° C., the conversion of the polysilane into silicon carbide is complete. Ceramic SiCN fibers are produced which have, for example a diameter of from 19 to 25 μm and are composed of 50 wt. % of silicon, 39 wt. % of carbon, 7 wt. % of nitrogen, 3 wt. % of oxygen and 1 wt. % of chlorine by elemental analysis.

The invention claimed is:
1. A polysilane produced by a process comprising the steps of:

performing a disproportionation reaction of a methylchlorodisilane mixture to produce a chlorine-containing oligosilane;

performing a substitution reaction of chlorine atoms contained in the chlorine-containing oligosilane by reacting with a primary amine; and performing a cross-linking reaction of the chlorine-containing oligosilane using a chain forming agent to produce polysilanes.

2. The polysilane according to claim 1, wherein:
the polysilane has a molecular weight Mw of from 1,000 to 10,000 g/mol; and
a bimodal molecular weight distribution and/or a polydispersity of from 1 to 5.

3. The polysilane according to claim 1, wherein the polysilane has a viscosity at 25° C. in a 50 wt. % solution in toluene of from 5 to 50 mPas.

4. The polysilane according to claim 1, wherein the polysilane can be spun during dry spinning with draft factors of from 5 to 10.

5. The polysilane according to claim 4, wherein a fiber filament reduction per hour has a value of from 0 to 75% during the dry spinning.

6. The polysilane according to claim 1, wherein the polysilane is soluble in toluene and/or dioxane in a concentration of from 70 to 90 wt. % and/or has a ceramic yield of at least 60% during pyrolysis up to 800° C.

7. The polysilane according to claim 1, wherein:
the polysilane has a molecular weight Mw of from 2,500 to 3,500 g/mol; and
a bimodal molecular weight distribution and/or a polydispersity of from 2.5 to 3.5.

8. The polysilane according to claim 4, wherein a fiber filament reduction per hour has a value of from 0 to 20% during the dry spinning.

9. Silicon carbide fibers produced by a process comprising the steps of:

producing polysilanes by a process containing the steps of:
performing a disproportionation reaction of a methylchlorodisilane mixture to produce a chlorine-containing oligosilane;
performing a substitution reaction of chlorine atoms contained in the chlorine-containing oligosilane by reacting with a primary amine;
performing a cross-linking reaction of the chlorine-containing oligosilane using a chain forming agent to produce the polysilanes;
spinning the polysilanes into polysilane fibers; and
converting the polysilane fibers into silicon carbide fibers by pyrolysis.

10. The silicon carbide fibers according to claim 9, wherein a cross-sectional surface of the silicon carbide fibers has an undulating boundary line.

11. A fiber composite material produced by a process comprising the steps of:
polysilane fibers produced by a process containing the steps of:
performing a disproportionation reaction of a methylchlorodisilane mixture to produce a chlorine-containing oligosilane;
performing a substitution reaction of chlorine atoms contained in the chlorine-containing oligosilane by reacting with a primary amine;
performing a cross-linking reaction of the chlorine-containing oligosilane using a chain forming agent to produce the polysilane fibers; and
transforming the polysilane fibers and a matrix material into a ceramic fiber composite material by pyrolysis.

12. The fiber composite material according to claim 11, which further comprises using the ceramic fiber composite material for lightweight construction, for electrical industry, for space travel, for automobile construction and for aircraft construction.

* * * * *